(12) United States Patent
Vink

(10) Patent No.: US 10,729,677 B2
(45) Date of Patent: *Aug. 4, 2020

(54) METHOD FOR PREVENTING AND/OR TREATING CHRONIC TRAUMATIC ENCEPHALOPATHY-I

(71) Applicant: EUSTRALIS PHARMACEUTICALS LIMITED, Melbourne, Victoria (AU)

(72) Inventor: Robert Vink, Mylor (AU)

(73) Assignee: EUSTRALIS PHARMACEUTICAL LIMITED (TRADING AS PRESSURA NEURO), Melbourne, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 14/902,239

(22) PCT Filed: Jul. 2, 2014

(86) PCT No.: PCT/AU2014/050107
§ 371 (c)(1),
(2) Date: Dec. 30, 2015

(87) PCT Pub. No.: WO2015/000032
PCT Pub. Date: Jan. 8, 2015

(65) Prior Publication Data
US 2016/0143881 A1    May 26, 2016

(30) Foreign Application Priority Data
Jul. 2, 2013   (AU) .............................. 2013902455

(51) Int. Cl.
*A61P 25/28* (2006.01)
*A61K 31/496* (2006.01)
*A61K 31/405* (2006.01)

(52) U.S. Cl.
CPC .......... *A61K 31/405* (2013.01); *A61K 31/496* (2013.01); *A61P 25/28* (2018.01)

(58) Field of Classification Search
CPC .............................. A61K 31/496; A61P 25/28
See application file for complete search history.

(56) References Cited

U.S. PATENT DOCUMENTS

| 2006/0247240 | A1* | 11/2006 | Hoffmann | A61K 31/435 514/235.2 |
| 2011/0053954 | A1 | 3/2011 | Hoffmann et al. | |
| 2011/0071135 | A1* | 3/2011 | Chase | A61K 31/166 514/215 |
| 2014/0193526 | A1* | 7/2014 | Henry | A61K 33/14 424/715 |
| 2014/0323393 | A1 | 10/2014 | Ruff | |
| 2016/0013160 | A1 | 1/2016 | Chun et al. | |

FOREIGN PATENT DOCUMENTS

| CA | 2831054 A1 | 12/2013 |
| WO | WO 2008/067610 A1 | 6/2008 |
| WO | WO 2009/009829 A1 | 1/2009 |

OTHER PUBLICATIONS

Saulle et al Chronic Traumatic Encephalopath: A Review) Rehabilitation Research and Practice, vol. 2012, p. 1-9, 2012.*
International Search Report dated Sep. 8, 2014 in application No. PCT/AU2014/050107.
Office Action dated Sep. 18, 2017 in U.S. Appl. No. 14/902,228.
Baugh et al., "Chronic traumatic encephalopathy: neurodegeneration following repetitive concussive and subconcussive brain trauma", Brain Imaging and Behavior (May 2012) vol. 6, pp. 244-254.
Franz et al., "Amyloid beta 1-42 and tau in cerebrospinal fluid after severe traumatic brain injury", Neurology (May 2013), vol. 60, No. 9, pp. 1457-1461.
Gao et al., "Chronic Traumatic Encephalopathy-like Neuropathological Findings without a History of Trauma," International Journal of Pathology and Clinical Research, (Jan. 2017) vol. 3(1) pp. 1-4.
Johnson et al., "Acute and Chronically Increased Immunoreactivity to Phosphorylation-Independent but Not Pathological TDP-43 After a Single Traumatic Brain Injury in Humans," Acta Neuropathol (Dec. 2011) vol. 122(6) pp. 715-726.
Office Action dated Feb. 22, 2018 in U.S. Appl. No. 14/902,228 (US 2016-013160).
Office Action dated Mar. 22, 2017 in U.S. Appl. No. 14/902,228 (US 2016-013160).
McKee et al., "The Neuropathology of Chronic Traumatic Encephalopahty," Brain Pathol. (May 2015) vol. 25, No. 3, pp. 350-364.
Tran et al., "Inhibition of JNK by a Peptide Inhibitor Reduces Traumatic Brain Injury-Induced Tauopathy in Transgenic Mice," J. Neuropathol Exp Neurol., (Feb. 2012) vol. 71, No. 2 pp. 116-129.
Donkin et al., "A Substance P Antagonist Reduces Axonal Injury and Improves Neurologic Outcome When Administered U to 12 Hours after Traumatic Brain Injury," Journal of Neurotrauma, vol. 28, pp. 217-224 (Feb. 2011).
Donkin et al, "Substance P is associated with the development brain edema and functional deficits after traumatic brain injury," Journal of Cerebral Blood Flow & Metabolism, vol. 29, pp. 1388-1398 (2009) (Published online May 2009).

(Continued)

*Primary Examiner* — Theodore R. West
(74) *Attorney, Agent, or Firm* — Foley & Lardner LLP

(57) ABSTRACT

The present invention relates to a method of preventing and/or treating chronic traumatic encephalopathy.

5 Claims, 5 Drawing Sheets

(56) References Cited

OTHER PUBLICATIONS

Gavett et al., "Mild traumatic brain injury: a risk factor for neurodegeneration," Alzheimer's Research & Therapy, vol. 2, No. 18, pp. 1-3 (2010).
McKee et al., "Chronic Traumatic Encephalopathy in Athletes: Progressive Tauopathy After Repetitive Head Injury," J. Neuropathol. Exp. Neurol., vol. 68, No. 7, pp. 709-735 (Jul. 2009).
Neal et al., "Concussions: What a neurosurgeon should know about current scientific evidence and management strategies," Surgical Neurology International, vol. 3, No. 16, pp. (Feb. 2015).
Thornton et al., "Treatment with a Substance P Receptor Antagonist Is Neuroprotective in the Intrastriatal 6-Hydroxydopamine Model of Early Parkinson's Disease," PLoS One, vol. 7, No. 4, e34138, pp. 1-8 (Apr. 2012).
Baylock et al., "Immunoexcitotoxicity as a central mechanism in chronic traumatic encephalopathy—A unifying hypothesis," Surg Nerurol Int. (2011) 2: 107 (Published online Jul. 30, 2011).
Office Action dated Jul. 31, 2019 in U.S. Appl. No. 14/902,228 (US 2016-0136160).
Office Action dated Apr. 8, 2020, in U.S. Appl. No. 14/902,228 (U.S. 2016-0136160).

* cited by examiner

METHOD FOR PREVENTING AND/OR TREATING CHRONIC TRAUMATIC ENCEPHALOPATHY-I

FIELD OF THE INVENTION

The present invention relates to a method of preventing and/or treating chronic traumatic encephalopathy.

BACKGROUND OF THE INVENTION

Concussion has become an important public health problem in the United States, Australia and elsewhere internationally. It is common in a number of contact sports including the Australian football codes such as AFL and NRL, ice hockey, American football, and boxing, amongst others. In the United States alone, over 300,000 sports related concussions occur annually and numbers are increasing worldwide (Ellenbogen et al., 2010, World Neurosurg. 74, 560-575). Concussive injuries are also a problem in the military and industrial worksites. In the case of the former, concussive injury resulting from exposure to the force of a detonation trigger similar neuropathological mechanisms leading to neuropathology and sequelae indistinguishable to chronic traumatic encephalopathy (Goldstein et al (2012) Sci. Transl. Med. 4(134): 1-16). Concussion causes no gross pathology, such as hemorrhage, and no abnormalities on structural brain imaging (McCrory et al., 2009, Phys. Sportsmed. 37, 141-159). There also may be no loss of consciousness, but many other complaints such as dizziness, nausea, reduced attention and concentration, memory problems, and headache have been reported. A greater likelihood of unconsciousness occurs with more severe concussions. These types of concussive head impacts are very frequent in American football whose athletes, especially linemen and linebackers, may be exposed to more than 1,000 impacts per season (Crisco et al., 2010, J. Athl. Train. 45, 549-559). The effects of multiple concussions are becoming better recognized in these professional footballers, but much less is known about the long term-effects of repeated concussion in the brains of amateur teenagers and adolescents. Moreover, the amateur codes of football are less regulated than the professional codes, and the adolescent brain may be more vulnerable to concussion. The better-developed neck musculature of the professional footballer, the more strictly controlled tackling and the better aftercare of the concussed professional means that the long-term public health problem of concussion in sport is grossly underestimated.

Military personnel who have experienced concussion experience a range of detrimental and chronic medical conditions. Concussion occurring among soldiers deployed in Iraq is strongly associated with PTSD and physical health problems 3 to 4 months after the soldiers return home. PTSD and depression are important mediators of the relationship between mild traumatic brain injury and physical health problems. PTSD was strongly associated with mild traumatic brain injury. It was reported that overall, 43.9% of soldiers who reported loss of consciousness met the criteria for PTSD, as compared with 27.3% of those with altered mental status, 16.2% of those with other injuries, and 9.1% of those with no injuries (Hoge et al, N Engl J Med. 2008; 358, 453-63). Also, more than 1 in 3 returning military troops who have sustained a deployment-related concussion have headaches that meet criteria for posttraumatic headache (Theeler et al., 2010, Headache: J Head and Face Pain 50, 1262-1272). It has been shown that nearly 15% of combat personnel sustained concussion whilst on duty (Hoge et al, N Engl J Med. 2008; 358, 453-63). Repeated concussion is a serious issue for combat personnel, with a study showing that a majority of concussion incidents were blast related. The median time between events was 40 days, with 20% experiencing a second event within 2 weeks of the first and 87% within 3 months (MacGregor et al, 2011, J Rehab Research and Develop, 48, 1269-1278). The impact of concussion and PTSD has resulted in a significant economic burden, (The Congress of the United States—Congressional Budget Office, The Veterans Health Administration's Treatment of PTSD and Traumatic Brain Injury Among Recent Combat Veterans, February 2012).

While an isolated concussion has been widely considered to be an innocuous event, recent studies (McKee et al., 2009, J Neuropath Exp Neurol 68, 709-735; Blennow et al., 2012, Neuron 76, 886-99) have suggested that repeated concussion is associated with the development of a neurodegenerative disorder known as chronic traumatic encephalopathy (CTE). CTE is regarded as a disorder that often occurs in midlife, years or decades after the sports or military career has ended (McKee et al., 2009, J Neuropath Exp Neurol 68, 709-735; Stem et al., 2011, Physical Med. Rehab. 3, 5460-7). About one-third of CTE cases are progressive, but clinical progression is not always sequential or predictable. The clinical symptoms vary extensively, which is probably due to varying, multiple damage sites amongst athletes with the condition (Stern et al., 2011, Physical Med. Rehab. 3, S460-7). The severity varies from mild complaints to severe deficits accompanied by dementia, Parkinson-like symptoms, and behavioral changes. Clinical symptoms include neurological and cognitive complaints together with psychiatric and behavioral disturbances. Early neurological symptoms may include speech problems and impaired balance, while later symptoms include ataxia, spasticity, impaired coordination, and extrapyramidal symptoms, with slowness of movements and tremor (Blennow et al., 2012, Neuron 76, 886-99; Stem et al., 2011, Physical Med. Rehab. 3, S460-7). Cognitive problems, such as attention deficits and memory disturbances, often become major factors in later stages of the disease, although may occur at varying times throughout the course of CTE. Psychiatric and behavioral problems include lack of insight and judgment, depression, disinhibition and euphoria, hypomania, irritability, aggressiveness and suicidal tendencies.

In post-mortem studies of athletes with CTE, the extensive presence of neurofibrillary tangles has been reported (McKee et al., 2009, J Neuropath Exp Neurol 68, 709-735; Stem et al., 2011, Physical Med. Rehab. 3, S460-7). Tangles are found intracellularly in the cytoplasm of neurons and consist of threadlike aggregates of hyperphosphorylated tau protein. Tau is a normal axonal protein that binds to microtubules via their microtubule binding domains, thus promoting microtubule assembly and stability. The hyperphosphorylated form of tau causes disassembly of microtubules and thus impaired axonal transport, leading to compromised neuronal and synaptic function, increased propensity of tau aggregation, and subsequent formation of insoluble fibrils and tangles. Unlike in Alzheimer's disease, tangles in athletes with CTE tend to accumulate perivascularly within the superficial neocortical layers, particularly at the base of the sulci. Tau pathology in CTE is also patchy and irregularly distributed, possibly related to the many different directions of mechanical force induced by physical trauma (McKee et al., 2009, J Neuropath Exp Neurol 68, 709-735). It is the accumulation of hyperphosphorylated tau protein that is thought to result in the development of CTE and its associated psychiatric and behavioral disturbances.

Given these psychiatric and behavioral disturbances in athletes with CTE, there is a clear need for a therapeutic intervention to prevent and/or treat chronic traumatic encephalopathy.

A reference herein to a patent document or other matter which is given as prior art is not to be taken as an admission that that document or matter was known or that the information it contains was part of the common general knowledge as at the priority date of any of the claims.

SUMMARY OF THE INVENTION

The present invention arises from studies into the association of substance P with tau hyperphosphorylation and development of chronic traumatic encephalopathy or a related condition having overlapping neuropathology and sequelae after concussive injury.

It is taught herein that the level of substance P is significantly increased following concussion. Substance P initiates tau hyperphosphorylation. It is prepared herein that substance P receptor antagonists are effective in reducing tau hyperphosphorylation thereby ameliorating the effects of CTE and related conditions.

Accordingly, in one aspect the present invention provides a method of preventing and/or treating chronic traumatic encephalopathy or a related condition in a subject, the method including administering to the subject an effective amount of a substance P receptor antagonist.

In another aspect, the present invention also provides use of a substance P receptor antagonist in the preparation of a medicament for preventing and/or treating chronic traumatic encephalopathy or a related condition in a subject.

In a further aspect the present invention also provides a pharmaceutical composition when used to treat chronic traumatic encephalopathy or a related condition, the composition including a substance P receptor antagonist.

In still a further aspect the present invention also provides a method of inhibiting progression of a disease, condition or state associated with tau hyperphosphorylation in a subject, the method including administering to the subject an effective amount of a substance P receptor antagonist.

In still a further aspect the present invention also provides use of a substance P receptor antagonist in the preparation of a medicament for inhibiting progression of a disease, condition or state associated with tau hyperphosphorylation in a subject, for instance a concussive injury.

In a further aspect the invention provides a method for treating a subject with a concussive injury, including the step of administering to said subject an effective amount of a substance P receptor antagonist.

In a further aspect the invention provides methods for treating psychiatric and behavioural problems associated with CTE in a subject in need thereof, including the step of administering to said subject an effective amount of a substance P receptor antagonist.

In an embodiment the psychiatric and behavioural problems are selected from the group consisting of depression, irritability, disinhibition and euphoria, hypomania, aggressiveness and suicidal tendencies.

In a further aspect the invention provides methods for treating cognitive problems associated with CTE, in a subject in need thereof, including the step of administering to said subject an effective amount of a substance P receptor antagonist.

In an embodiment the cognitive problems associated with CTE are selected from the group consisting of attention deficits and memory disturbances.

Various terms that will be used throughout the specification have meanings that will be well understood by a skilled addressee. However, for ease of reference, some of these terms will now be defined.

The term "chronic traumatic encephalopathy (CTE)" as used throughout the specification is a condition appearing in response to repeated concussion resulting in accumulation of neurofibrillary tangles consisting of hyperphosphorylated tau protein. The perivascular appearance of these neurofibrillary tangles within the superficial neocortical layers, and particularly at the base of the sulci, is unique to athletes and has been associated with the subsequent development of psychiatric and behavioral disturbances.

The term "tau hyperphosphorylation" as used throughout the specification is to be understood to mean the phosphorylated form of tau that causes disassembly of microtubules and thus impaired axonal transport, leading to compromised neuronal and synaptic function, increased propensity of tau aggregation, and subsequent formation of insoluble fibrils and tangles.

In this regard, a disease condition or state known as chronic traumatic encephalopathy is associated with accumulation of hyperphosphorylated tau protein, leading to compromised neuronal and synaptic function, increased propensity of tau aggregation, subsequent formation of insoluble fibrils and tangles, and the development of psychiatric and behavioral disturbances.

A related condition is a condition having overlapping neuropathology and sequelae.

The term "substance P receptor antagonist" as used throughout the specification is to be understood to mean an agent that directly or indirectly inhibits the binding of substance P to one of its receptors. In this regard, it will be appreciated that a substance P receptor antagonist includes a derivative, a variant, an analogue, a pharmaceutically acceptable salt, a solvate, a tautomer or a pro-drug of a substance P receptor antagonist.

In this regard, substance P is an excitatory neurotransmitter and is a peptide having the structure RPKPEEFFGLM-NH$_2$ (SEQ ID NO 1). Methods for determining the ability of an agent to act as a substance P receptor antagonist are known in the art (Cascieri et al., 1983, J Biol Chem 258, 5158).

The term "variant" as used throughout the specification is to be understood to mean an amino acid sequence of a polypeptide or protein that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids. The term also includes within its scope any insertions/deletions of amino acids for a particular polypeptide or protein. A "functional variant" will be understood to mean a variant that retains the functional capacity of a reference protein or polypeptide.

Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Under some circumstances, substitutions within the aliphatic group alanine, valine, leucine and isoleucine are also considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Substitutions as described above are contemplated within the scope of the present invention.

The term "prevent" as used throughout the specification is to be understood to mean an intervention that prevents or delays the onset of a disease, condition or state in a subject. The term "treat" as used throughout the specification is to be understood to mean an intervention that improves the prognosis and/or state of a subject with respect to a disease, condition or state.

The term "subject" as used throughout the specification is to be understood to mean a human or animal subject.

The present invention furthermore has military applications such as administering a substance P antagonist at an aid station shortly after a blast injury or traumatic events involving the head or during post recovery.

It will also be understood that the present invention further includes within its scope veterinary applications. For example, the animal subject may be a mammal, a primate, a livestock animal (eg. a horse, a cow, a sheep, a pig, or a goat), a companion animal (eg. a dog, a cat), a laboratory test animal (eg. a mouse, a rat, a guinea pig, a bird, a rabbit), an animal of veterinary significance, or an animal of economic significance.

GENERAL DESCRIPTION OF THE INVENTION

Figure 1:
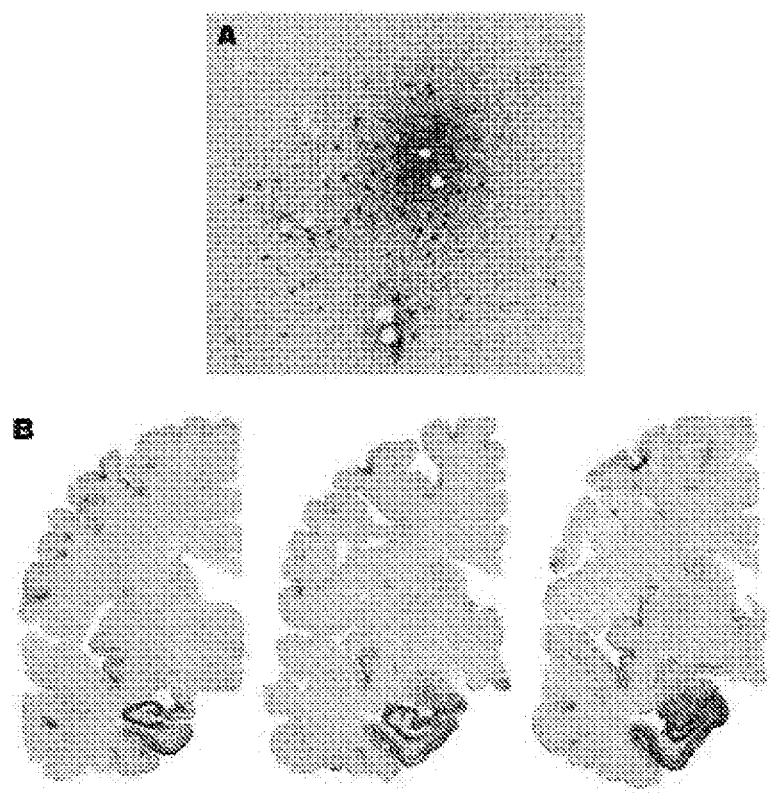
FIG. 1 shows immunohistology using antibody for phosphorylated tau of sections of a human brain diagnosed with CTE demonstrating the perivascular appearance (A) of hyperphosphorylated tau within the superficial neocortical layers, and particularly at the base of the sulci (B) (from McKee et al, 2009, J Neuropath Exp Neurol 68, 709-735).

As described above, the present invention provides a method of preventing and/or treating chronic traumatic encephalopathy or a related condition in a subject, the method including administering to the subject an effective amount of a substance P receptor antagonist.

This embodiment of the present invention is directed to preventing and/or treating a disease, condition or state associated with tau hyperphosphorylation by administering to a subject one or more substance P receptor antagonists.

Tau hyperphosphorylation may be induced by a variety of reasons, including for example, a concussive event or a mechanical impact that activates brain mechanoreceptors. In this regard, tau hyperphosphorylation may be associated, for example, with either or both an accumulation of hyperphosphorylated tau over time as measured within the one subject, or may be an accumulation of hyperphosphorylated tau in one subject compared to the accumulation of hyperphosphorylated tau in a population.

Diseases, conditions or states associated with accumulation of hyperphosphorylated tau in a subject in the various embodiments of the present invention include chronic traumatic encephalopathy (CTE).

Chronic traumatic encephalopathy (CTE) is normally classified as a disease associated with accumulation of tangles containing hyperphosphorylated tau, with these tangles tending to accumulate perivascularly within the superficial neocortical layers, particularly at the base of the sulci. There is currently no blood or laboratory test that is definitive for the diagnosis of CTE, with disease confirmation usually occurring after postmortem examination of brain tissue. Nonetheless, a number of clinical criteria plus a history of concussive events in the subject are usually sufficient in making a tentative diagnosis. In this regard, the Diagnostic and Statistical Manual of Mental Disorders (American Psychiatric Association) is commonly used to assess a number of parameters to provide an indication of the presence and severity of CTE in a subject. Nuclear medical imaging, including Positron Emission Tomography (PET), may also be used to assess the presence and severity of CTE. Methods of assessing CTE in a subject using PET include for example Small et al. (2013) *Am. J. Geriatr. Psychiatry.* 21: 138-144.

Accordingly, in a further embodiment the invention may include a CTE diagnostic step which may be performed by injecting the subject with a PET molecular imaging probe (to visualise CTE in living humans). Such imaging probes are known, for instance, FDDNP(2-1-{6-[(2-[F-18]fluoroethyl) (methyl)amino]-2-napthyl}ethylidene)malononitrile. Such probes are able to visualise tau tangles.

In a further embodiment the diagnostic step may include an assessment of the plasma levels of total tau (T-tau) using an immunoassay for instance, as described in Rissen et al, Nature Biotechnology 2010; 28:595-599 (which is incorporated by reference in its entirety).

In an embodiment diagnosis of CTE may be made based on a plasma level of Tau (based on the aforementioned assay) of above 1.5 $ngL^{-1}$, for instance, above 1.6, above 1.7, above 1.8, above 1.9, above 2.0, above 2.1, above 2.2, above 2.3, above 2.4, above 2.5, above 2.6, or above 2.7 $ngL^{-1}$.

In one specific embodiment, the disease, condition or state associated with accumulation of hyperphosphorylated tau is chronic traumatic encephalopathy.

In another specific embodiment, the diverse, condition or state associated with accumulation of hyperphosphorylated tau is a concussive event or injury.

Substance P binds to a number of receptors including the NK1 receptor (neurokinin 1 receptor), the NK2 receptor and the NK3 receptor. Substance P antagonists inhibit the binding of substance P to any one of its receptors. Accordingly, NK1, NK2, and NK3 receptor antagonists will also function as substance P receptor antagonists. It will be appreciated that the term "substance P" includes within its scope various variants, truncated forms or analogues of the peptide, for example as described in U.S. Pat. No. 4,481,139.

The identification of a substance as a substance P receptor antagonist may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). The method involves determining the concentration of the individual compound required to reduce by 50% the amount of radiolabelled substance P ligands at their receptor sites in said isolated bovine thereby affording characteristic $IC_{50}$ values for each compound tested.

TABLE 1

| NK1 Receptor Antagonists | |
|---|---|
| Chemical Code | Chemical Name |
| Casopitant | (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide |
| CGP49823 | (2R,4S)-2-benzyl-1-(3,5-dimethylbenzoyl)-N-[(4-quinolinyl)methyl]-4-piperineamine) dihydrochloride |
| CP-122,721 | (+)-2S,3S)-3-(2-methoxy-5-trifluoromethoxybenzyl)amino-2-phenylpiperidine |
| CP-96,345 | 2S,3S)-cis-(2-(diphenylmethyl)-N-[(2-methoxyphenyl)methyl]-1-azabicyclo[2.2.2]octan-3-amine |
| CP-99,994 | ((2S,3S)-cis-3-(2-methoxybenzylamino)-2-phenyl-piperidine)dihydrochloride |
| FK 888 | (N2-[(4R)-4-hydroxy-1-(1-methyl-1H-indol-3-yl)carbonyl-L-propyl\-N-methyl-N-phenylmethyl-L-3-(2-napthyl)-alaninamide |
| GR 82334 | [D-Pro9,)spiro-gamma-lactam]Leu10, Trp11] physalaemin-(1-11) |
| GR 94800 | PhCO-Ala-Ala-DTrp-Phe-DPro-Pro-Nle-NH2 |
| GR203040 | (2S,3S and 2R,3R)-2-methoxy-5-tetrazol-1-yl-benzyl-(2-phenyl-piperidin-3-yl)-amine |
| GR-205171 | 3-Piperidinamine,N-[[2-methoxy-5-[5-(trifluoromethyl)-1H-tetrazol-1yl]phenyl]methyl]-2-phenyl, (2S-cis)- |
| GSK1144814 | Unknown |
| GSK206136 | Unknown |
| GSK424887 | Unknown |
| GW679769 | Unknown |
| HSP-117 | 3-Piperidinamine, N-[[2,3-dihydro-5-(1-methylethyl-7-benzofuranyl]methyl)2-phenyl-, dihydrochloride, (2S-cis)- |
| L 703,606 | 1-Azabicycio[2.2.]octan-3-amine, 2-(diphenylmethyl)-N-[(2-idophenyl)methyl]-, (2S-cis)-, oxalate |
| L 732,138 | N-acetyl-L-tryptophan |
| L 733,060 | ((2S,S)-3-((3,5-bis(trifluoromethyl)phenyl)methyloxy)-2-phenyl piperidine |
| L 742,694 | (2-(S)-(3,5-bis(trifluromethyl)benzyloxy)-3-(S)-phenyl-4-(5-(3-oxo-1,2,4-triazolo)methylmorpholine |
| L668,169 | L-Phenylalanine, N-[2-[3-[[N-[2-(3-[(N-[2-[3-amine-2-oxo-1-pyrrolidinyl]-4-methyl-1-oxopentyl]-L-methionyl-L-glutaminyl-D-tryplophyl-N-methyl-L-phenylalanyl]amino]-2-oxo-1-pyrrolidinyl]-4-methyl-1-oxopentyl]-L-methionyl-L-glutaminyl-D-tryptophyl-N-methyl-,cyclic (8->1)-peptide, [3R-[1[S*[R*(S*)]], 3R*]]- |
| LY 303241 | 1-Piperazineacetamide, N-[2-[acetyl[(2-methoxyphenyl)methyl]amine]-1-(1H-indol-3-ylmethyl)(ethyl]-4-phenyl-, (R)- |
| LY 303870 | (R)-1-[N-(2-methoxybenzyl)acetylamino]-3-(1H-indol-3-yl)-2-[N-(2-(4-(pi peridinyl)piperidin-1-yl)acetyl)amino]propane |
| LY 306740 | 1-Piperazineacetamide, N-[2-'acetyl[(2-methoxypehenyl)methyl]amino]-1-(1H-indol-3-ylmethyl)ethyl]-4-cyclohexyl-, (R)- |
| Maropitent | (7R,8S)-N-[(5-tert-Butyl-2-methoxyphenyl)methyl]-7-[di(phenyl)methyl]-1-azabicyclo[2.2.2]octan-8-amine |
| MEN 11149 | 2-(2-naphthyl)-1-N[(1R,2S)-2-N-[1(H)indol-3-ylcarbonyl]aminocyclohexanecarbonyl]-1-[N'-ethyl-N'-(4-methylphenylacetyl)] diaminoethane |
| Orvepitant | (2R,4S)-N-((R)-1-(3,5-bis(trifluromethyl)phenyl)ethyl)-2-(4-fluoro-2-methylphenyl)-N-methyl-4-((S)-6-oxohexahydropyrrolo[1,2-a]pyrazin-2(1H)-yl)piperidine-1-carboxamide maleate |
| PD 154075 | (2-benzofuran)-CH2OCO]—(R)-alpha-MeTrp-(S)—NHCH(CH3)Ph |
| R-544 | Ac-Thr-D-Trp(FOR)-Phe-N-MeBzl |
| RP-67580 | (3aR,7aR)-7,7-diphenyl-2[1-imino-2(2-methoxyphenyl)-(ethyl]+++perhydroisoindol-4-one hydrochloride |

TABLE 1-continued

NK1 Receptor Antagonists

| Chemical Code | Chemical Name |
|---|---|
| RPR 100893 | (3aS,4S,7aS)-7,7diphenyl-4-(2-methoxyphenyl)-2-[(S)-2-(2-methoxyphenyl)proprionyl]perhydroisoindol-4-ol |
| SCH619734 | (5S)-8(S)-[[1(R)-[3,5 bis(trifluoromethyl)phenyl]ethoxy]methyl]-8-phenyl-1,7-diazaspiro[4,5]decan-2-one) |
| Spantide II | D-NicLys1, 3-Pal3, D-Cl2Phe5, Asn6, D-Trp7.0, Nle11-substance P |
| Spantide III | L-Norleucinamide, N6-(3-pyridinylcarbonyl)-D-lysyl-L-prolyl-3-(3-pyridinyl)-L-alanyl-L-prolyl-3,4-dichioro-D-phenylalanyl-L-asparaginyl-D-tryptophyl-L-phenylalanyl-3-(3-pyridinyl)-D-alanyl-L-leucyl- |
| Spendide | Tyr-D-Phe-Phe-D-His-Leu-Met-NH2 |
| SR140333 | (S)-1-[2-[3-(3,4-dichlorphenyl)-1 (3-isopropoxyphenylacetyl) piperidin-3-yl] ethyl]-4-phenyl-1 azaniabicyclo [2.2.2]octane |
| Vestipitant | (2S)-N-[(1R)-1-[3,5-bis(trifluoromethyl)phenyl]ethyl]-2-(4-fluoro-2-methylphenyl)-N-methylpiperazine-1-carboxamide |
| WIN-41,708 | (17beta-hydroxy-17alpha-ethynyl-5alpha-androstano[3,2-b]pyrimido[1,2-a]benzimidazole |
| WIN-62,577 | 1H-Benzimidazo[2,1-b]cyclopenta[5,6]naphtha[1,2-g]quinazolin-1-ol, 1-ethynyl-2,3,3a,3b,4,5,15,15a,15b,16,17,17a-dodeachydro-15a, 17a-dimethyl-,(1R,3aS,3bR,15aR,15bS,17aS)- |

TABLE 2

NK2 Receptor Antagonists

| Chemical Code | Chemical Name |
|---|---|
| SR-48,968 | (S)-N-methyl-N[4-(4-acetylamino-4-[phenylpiperidine)-2-(3,4-dichlorophenyl)-butyl]benzamide |
| L-659,877 | Cyclo[Gin,Trp,Phe,Gly,Leu,Met] |
| MEN 10627 | Cyclo(Met-Asp-Trp-Phe-Dap-Leu)cyclo(2beta-5beta) |
| SR 144190 | (R)-3-(1-[2-(4-benzoyl-2-(3,4-difluorophenyl)-morpholin-2-yl)-ethyl]-4-phenylpiperidin-4-yl)-1-dimethylurea |
| GR 94800 | PhCO-Ala-Ala-D-Trp-Phe-D-Pro-Pro-Nle-NH2 |

TABLE 3

NK3 Receptor Antagonists

| Chemical Code | Chemical Name |
|---|---|
| SR-142,801 | (S)-(N)-(1-(3-(1-benzoyl-3-(3,4-dichlorophenyl)piperidin-3-yl)propyl)-4-phenylpiperidin-4-yl)-N-methyl acetaide |
| R820 | 3-Indolylcarbonyl-Hyp-Phg-N(Me)-Bzl |
| R486 | H-Asp-Ser-Phe-Trp-beta-Ala-Leu-Met-NH2 |
| SB 222200 | (S)-(−)-N-(a-ethylbenzyl)-3-methyl-2-phenylquinoline-4-carboximide |
| L 758,298 | Phosphonic acid, [3-[[2-[1-[3,5-bis(trifluoromethyl)phenyl]ethoxy]-3-(4-fluorophenyl)-4-morpholinyl]methyl]-2,5-dihydro-4oxo-1H-1,2,4-triazol-1-yl]-, [2R-[2a(R*), 3a]]- |
| NK-608 | (2R,4S)-N-[1-[3.5-bis(trifluormethyl)-benzoyl]-2-(4-chloro-benzyl)-4-piperidinyl]-quinoline-4-carboxamide |

Other examples of substance P receptor antagonists are as described in U.S. Pat. Nos. 4,481,139 and 5,977,104. Examples of NK1 receptor antagonists are as described in U.S. Pat. No. 5,990,125.

In one embodiment, the substance P receptor antagonist is one or more of a NK1 receptor antagonist, a NK2 receptor antagonist, and a NK3 receptor antagonist.

In one embodiment, the NK1 receptor antagonist is selected from one or more of the group consisting of Casopitant, CGP49823, CP-122,721, CP-96,345, CP-99, 994, FK 888, GR 82334, GR 94800, GR203040, GR-205171, GSK1144814, GSK206136, GSK424887, GW679769, HSP-117, L 703,606, L 732,138, L 733,060, L 742,694, L668,169, LY 303241, LY 303870, LY 306740, Maropitant, MEN 11149, Orvepitant, PD 154075, R-544, RP-67580, RPR 100893, SCH619734, Spantide II, Spantide III, Spendide, SRI 40333, Vestipitant, WIN-41,708, WIN-62,577, or a derivative, a variant, an analogue, a pharmaceutically acceptable salt, solvate, tautomer or pro-drug thereof.

In another embodiment, the NK2 receptor antagonist is selected from one or more of the group consisting of SR-48968, L-659877, GR103537, MGN-10627, SR144190 and GR94800, or a derivative, a variant, an analogue, a pharmaceutically acceptable salt, tautomer or pro-drug thereof.

In another embodiment, the NK3 receptor antagonist is selected from one or more of the group consisting of SR-143,801, R820, R486, SB222200, L758,298 and NKP608, or a derivative, a variant, an analogue, a pharmaceutically acceptable salt, tautomer or pro-drug thereof.

In one embodiment, the substance P receptor antagonist is L-732,138, namely N-acetyl-L-tryptophan, or a derivative, analogue, pharmaceutically acceptable salt, solvate, tautomer or pro-drug thereof. Examples include lipid soluble analogues, N-acetyl-L-tryptophan 3,5-bis(trifluoromethyl) benzyl ester and N-acetyl tryptophan methyl ester.

One or more substance P receptor antagonists may also be used in the preparation of a medicament for preventing and/or treating chronic traumatic encephalopathy or a related condition.

Accordingly, in another embodiment the present invention provides use of a substance P receptor antagonist in the preparation of a medicament for preventing and/or treating chronic traumatic encephalopathy or a related condition.

One or more substance P receptor antagonists may also be used in a pharmaceutical composition, to prevent and/or treat chronic traumatic encephalopathy or a related condition.

Accordingly, in another embodiment the present invention provides a pharmaceutical composition when used to prevent and/or treat chronic traumatic encephalopathy or a related condition, the composition including a substance P receptor antagonist.

The administration of one or more substance P receptor antagonists may also be used to inhibit progression of the disease, condition or state associated with chronic traumatic encephalopathy or a related condition in the subject.

Accordingly, in another embodiment the present invention provides a method of inhibiting progression of chronic traumatic encephalopathy or a related condition, the method including administering to the subject an effective amount of a substance P receptor antagonist.

The effective amount of a substance P receptor antagonist to be delivered in the various embodiments of the present invention is not particularly limited, so long as it is within such an amount and in such a form that generally exhibits a useful or therapeutic effect. The term "effective amount" is the quantity which when delivered, improves the prognosis of the subject. The amount to be delivered will depend on the particular characteristics of the condition being treated, the mode of delivery, and the characteristics of the subject, such as general health, other diseases, age, sex, genotype, body weight and tolerance to drugs.

In an embodiment, an effective amount of a substance P receptor antagonist is an amount to be delivered to restore plasma levels of total tau (T-tau) (for instance by the immunoassay identified hereinbefore) to less than 1 $ngL^{-1}$, for instance, less than 0.9 $ngL^{-1}$, or less than 0.8 $ngL^{-1}$. This may involve a single dose or repeated dosages.

Accordingly, a suitable dosage of the substance P receptor antagonist for delivery to the desired site of action in the various embodiments of the present invention may be selected.

In an embodiment the method relates to a method for treating a concussive injury which involves a patient being exposed to multiple (more than one) concussive events. In such a method, the attendant physician would determine that the subject is concussed and that the subject has had at least one previous concussion. Methods for determining whether or nor a subject has been concussed includes for instance a variety of neuropsychological assessment tools (Kelly et al., 2012, Arch Clin Neuropsycho 27, 375-88; Echemendia et al., 2012, Clin Neuropsychol 26, 1077-91). However, the detection of loss of memory, an alteration of mental state (mental cloudiness, headache, dizziness, confusion, disorientation), possible loss of consciousness, or focal neurological deficits is more commonly used for on-field diagnosis of a concussive event. Other diagnostic criteria are outlined in detail in the American Society for Sports Medicine position statement (Br J Sports Med, 2013, 47, 15-26) and are summarised on the regularly updated Centres for Disease Control and Prevention (USA) website (http://www.cdc.gov/concussion/sports/index.html). Once this has been established the physician would then administered an effective amount of a substance P receptor antagonist.

In one embodiment, the dosage of the substance P receptor antagonist administered to a subject in the various embodiments of the present is in the range from 0.1 mg/kg to 100 mg/kg.

In a specific embodiment, the substance P receptor antagonist is administered to the subject at a dose of 0.25 mg/kg to 25 mg/kg. For example, a suitable dose of N-acetyl-tryptophan is 2.5 mg/kg.

In an embodiment the effective amount is an amount which is able to maintain the blood concentration of the substance P receptor antagonist in the therapeutic range for at least 3 days, for instance at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, or at least 20 days.

In an embodiment the effective amount is administered as a single dose.

In an embodiment the effective amount is administered as a single oral dose.

Accordingly, in another aspect the invention provides a method for treating a subject which has been exposed to multiple concussive events including the step of administering to the subject a substance P receptor antagonist as a single oral dose in an amount which is able to maintain the blood concentration of the substance P receptor antagonist in the therapeutic range for at least 3 days, wherein the administration step is performed after the second concussive event and again after each additional concussive event as required.

In an embodiment the substance P receptor antagonist is administered within 24 hours of the concussive event.

In an embodiment administration is provided within 20 hours such as within, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours and within 1 hour, of the concussive event.

In an embodiment the oral dose is in the form of a tablet, capsule, drink solutions or parenteral.

Generally, the dosage of the substance P receptor antagonist in a pharmaceutical composition may be in the range from 10-5,000 mg per subject, and typically will be in the range of 50-2,000 mg per subject.

Suitable dosages are generally as described in U.S. Pat. Nos. 4,990,125 and 5,977,104 (incorporated within by reference in its entirety).

Examples of formulations are described in U.S. Pat. No. 5,990,125 (incorporated within by reference in its entirety).

Methods for the preparation of pharmaceutical compositions are known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

As discussed previously herein, administration and delivery of the compositions may be for example by the intravenous, intraperitoneal, subcutaneous, intramuscular, oral, or topical route, or by direct injection. The mode and route of administration in most cases will depend on the severity and frequency of the concussive events.

The dosage form, frequency and will depend on the mode and route of administration.

As described above, the administration of the substance P receptor antagonist and other agents may also include the use of one or more pharmaceutically acceptable additives, including pharmaceutically acceptable salts, amino acids, polypeptides, polymers, solvents, buffers, excipients, preservatives and bulking agents, taking into consideration the particular physical, microbiological and chemical characteristics of the agents to be administered.

For example, the substance P receptor antagonist and/or the other agents can be prepared into a variety of pharmaceutically acceptable compositions in the form of, e.g., an aqueous solution, an oily preparation, a fatty emulsion, an emulsion, a lyophilised powder for reconstitution, etc. and can be administered as a sterile and pyrogen free intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, caplets, capsules, granules or powders; liquid preparations such as syrup, emulsions, dispersions or suspensions).

Compositions containing the substance P receptor antagonist and/or the other agents may also contain one or more pharmaceutically acceptable preservatives, buffering agents, diluents, stabilisers, chelating agents, viscosity enhancing agents, dispersing agents, pH controllers, or isotonic agents.

Examples of suitable preservatives are benzoic acid esters of para-hydroxybenzoic acid, propylene glycol, phenols, phenylethyl alcohol or benzyl alcohol. Examples of suitable buffers are sodium phosphate salts, citric acid, tartaric acid and the like. Examples of suitable stabilisers are, antioxidants such as alpha-tocopherol acetate, alpha-thioglycerin, sodium metabisulphite, ascorbic acid, acetylcysteine, 8-hydroxyquinoline, chelating agents such as disodium edetate. Examples of suitable viscosity enhancing agents, suspending or dispersing agents are substituted cellulose ethers, substituted cellulose esters, polyvinyl alcohol, polyvinylpyrrolidone, polyethylene glcols, carbomer, polyoxypropylene glycols, sorbitan monooleate, sorbitan sesquioleate, polyoxyethylene hydrogenated castor oil 60.

Examples of suitable pH controllers include hydrochloric acid, sodium hydroxide and the like. Examples of suitable isotonic agents are glucose, D-sorbitol or D-mannitol, sodium chloride.

The administration of a substance P receptor antagonist and/or the other agents in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, glidant, anti-adherant, binder, flavorant or sweetener, taking into account the physical, chemical and microbiological properties of the agents being administered.

For these purposes, the composition may be administered orally, parenterally, by inhalation spray, adsorption, absorption, topically, rectally, nasally, mucosally, transdermally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the compositions will normally be in a unit dosage, sterile, pyrogen free injectable form (solution, suspension or emulsion, which may have been reconstituted prior to use), which is generally isotonic with the blood of the recipient with a pharmaceutically acceptable carrier. Examples of such sterile injectable forms are sterile injectable aqueous or oleaginous suspensions. These suspensions may be formulated according to techniques known in the art using suitable vehicles, dispersing or wetting agents and suspending agents. The sterile injectable forms may also be sterile injectable solutions or suspensions in non-toxic parenterally acceptable diluents or solvents, for example, as solutions in 1,3-butanediol. Among the pharmaceutically acceptable vehicles and solvents that may be employed are water, ethanol, glycerol, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

In addition, the compositions may be in a form to be reconstituted prior to administration. Examples include lyophilisation, spray drying and the like to produce a suitable solid form for reconstitution with a pharmaceutically acceptable solvent prior to administration.

Compositions may include one or more buffers, bulking agents, isotonic agents and cryoprotectants and lyoprotectants. Examples of excipients include, phosphate salts, citric acid, non-reducing such as sucrose or trehalose, polyhydroxy alcohols, amino acids, methylamines, and lyotropic salts which are usually used instead of reducing sugars such as maltose or lactose.

When administered orally, the substance P receptor antagonist will usually be formulated into unit dosage forms such as tablets, caplets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include excipients such as lactose, dextrose, sucrose, sorbitol, mannitol, starches, gum acacia, calcium phosphate, mineral oil, cocoa butter, oil of *theobroma*, alginates, tragacanth, gelatin, syrup, substituted cellulose ethers, polyoxyethylene sorbitan monolaurate, methyl hydroxybenzoate, propyl hydroxybenzoate, talc, magnesium stearate, and the like.

A tablet may be made by compressing or molding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the substance P receptor antagonist may also utilize controlled release technology.

The substance P receptor antagonist may also be administered as a sustained-release pharmaceutical composition. To further increase the sustained release effect, the agent may be formulated with additional components such as vegetable oil (for example soybean oil, sesame oil, *camellia* oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof, carboxymethylcellulose sodium hydroxypropylcellulose ether, collagen polyethylene glycol polyethylene oxide, hydroxypropylmethylcellulosemethylcellulose, polyvinyl alcohol, polyvinylpyrrolidone.

Alternatively, the substance P receptor antagonist may be incorporated into a hydrophobic polymer matrix for controlled release over a period of days. The agent may then be moulded into a solid implant, or externally applied patch, suitable for providing efficacious concentrations of the agents over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers, which may be used externally or internally. Certain hydrogels such as poly (hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time-release characteristics and release kinetics. The agent may then be moulded into a solid implant suitable for providing efficacious concentrations of the agents over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the substance P receptor antagonist may be in the form of a solution, spray, lotion, cream (for example a non-ionic cream), gel, paste or ointment. Alternatively, the composition may be delivered via a liposome, nanosome, rivosome, or nutri-diffuser vehicle.

It will be appreciated that other forms of administration of agents are also contemplated, including the use of a nucleic acid encoding a polypeptide for delivering of such agents.

DESCRIPTION OF SPECIFIC EMBODIMENTS

Reference will now be made to experiments that embody the above general principles of the present invention. However, it is to be understood that the following description is not to limit the generality of the above description.

Example 1

Concussion Results in Accumulation of Hyperphosphorylated Tau

A number of clinical and experimental studies have now shown that there is an accumulation of hyperphosphorylated tau following concussive injury. Accumulation of neurofibrillary tangles containing hyperphosphorylated tau is a hallmark pathology of chronic traumatic encephalopathy, especially when this accumulation is perivascular and predominantly found within the superficial neocortical layers, particularly at the base of the sulci. In human studies (McKee et al., 2009, J Neuropath Exp Neurol 68, 709-735) such a distribution of hyperphosphorylated tau is readily apparent in subjects who have a history of repeated concussive events (FIG. 1). In this particular example, localization of hyperphosphorylated tau is shown in an NFL football player with a history of repeated concussion. Note the perivascular localization of hyperphosphorylated tau (A) with highest accumulations at the base of the sulci. This pathology is unique to chronic traumatic encephalopathy. Similar accumulations of hyperphosphorylated tau have been shown following experimental concussion in animals, although the absence of sulci in the experimental animals used in these studies to date has precluded the demonstration that such accumulation replicates the human pattern of localisation at the base of the sulci.

Example 2

Concussion Results in Perivascular Substance P Release

Figure 2:
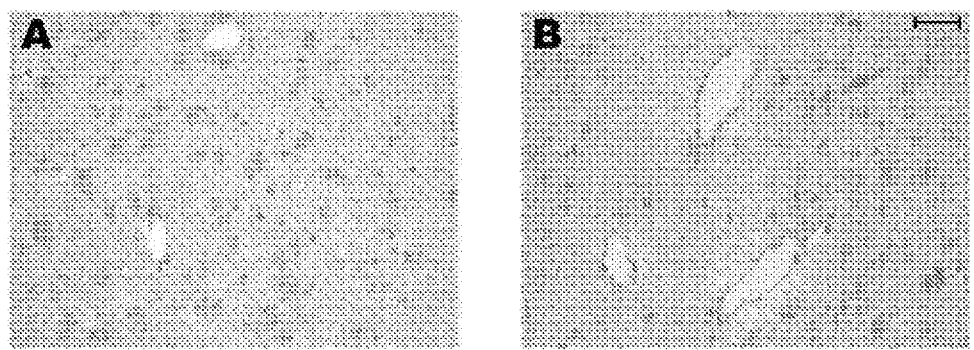
FIG. 2 shows substance P immunoreactivity in normal (A) and injured rats (B) at 3 days following mild concussive injury (B). In the injured animals, note the darkly stained, perivascular substance P positive axons and the presence of substance P positive neurones after injury (B) Bar—100 µm.

Having established that hyperphosphorylated tau accumulates perivascularly following concussive injury, we used an animal model of concussion to investigate whether concussion causes perivascular release of substance P. We developed a rodent model of concussion to replicate the concussive event (Donkin et al., 2004, *7th International Neurotrauma Symposium*, pp 75-78, Medimond Publishers, Bologna, Italy) and subsequently determined whether substance P was released after such an event. There was a clear increase in brain perivascular substance P immunoreactivity after the concussive event (FIG. 2). We propose that mechanical stimulation of sensory nerve fibres was responsible for this perivascular release of substance P. These results are consistent with previous studies in non-brain tissue demonstrating that mechanical stimulation of sensory nerve fibres induces substance P release (Ang et al., 2011, PLoS One 6, e24535).

Example 3

Administration of a NK1 Receptor Antagonist Prevents Tau Phosphorylation

Figure 3:
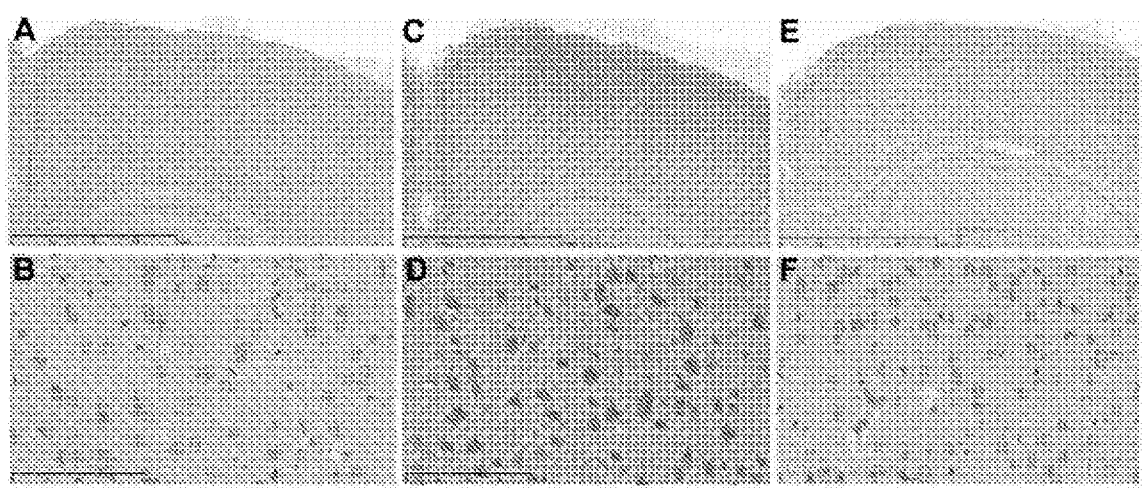
FIG. 3 shows the effects of a NK1 receptor antagonist (n-acetyl-L-tryptophan) on tau phosphorylation after concussive injury. Note that concussive injury in the rat causes extensive tau phosphorylation (CD) by 3 days after the concussive event compared to non-injured animals (A,B). The administration of an NK1 receptor antagonist (n-acetyl-L-tryptophan) at 30 min after the induction of injury results in almost complete inhibition of tau phosphorylation at this 3 day time point (E,F).

Having shown that mechanical injury causes release of substance P after concussive injury, we then investigated whether a substance P NK1 receptor antagonist reduces tau hyperphosphorlation after concussive injury. FIG. 3 shows the effects of an NK1 receptor antagonist (n-acetyl-L-tryptophan) on tau phosphorylation after concussive injury. Note that concussive injury in the rat causes extensive tau phosphorylation (C,D) by 3 days after the concussive event compared to non-injured animals (A,B). The administration of the NK1 receptor antagonist at 30 min after the induction of injury results in almost complete inhibition of tau phosphorylation at this 3 day time point (E,F). Thus, administration of an NK receptor antagonist prevents tau hyperphosphorylation and thus prevents the development of CTE.

Example 4

The Mechanism by which Substance P Antagonists Inhibit Tu Hyperphosphorylation

Figure 4:
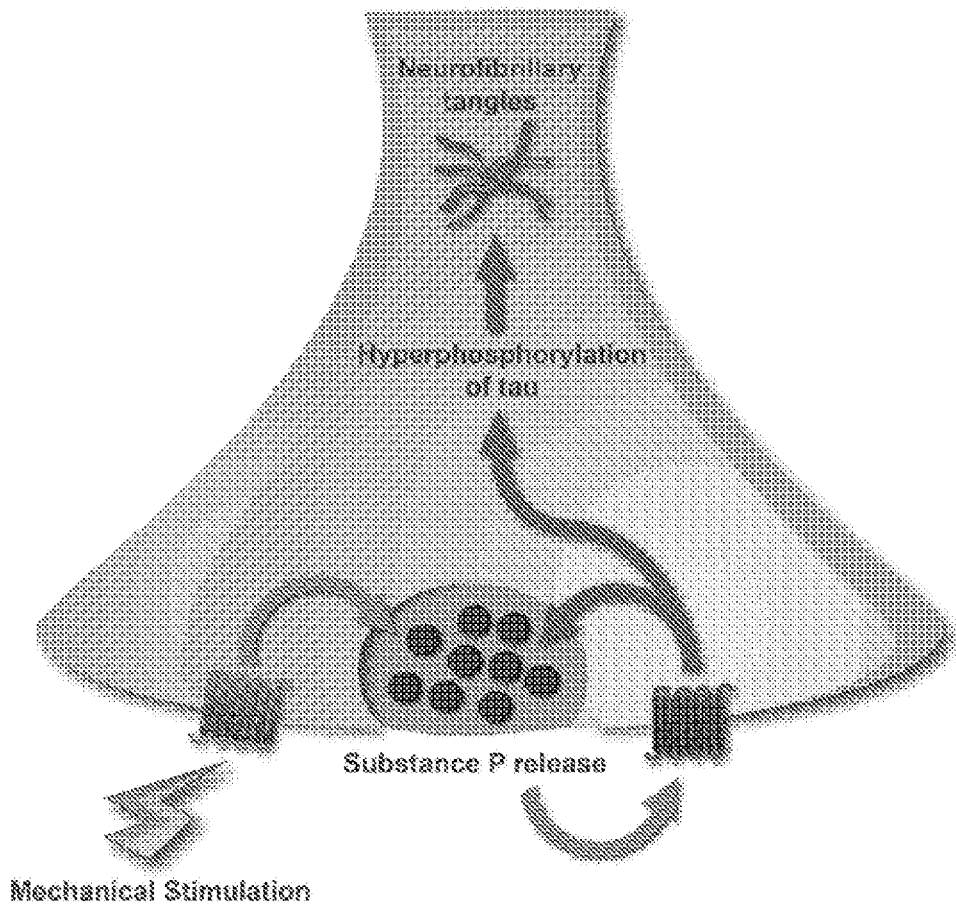
FIG. 4 shows a schematic model of how concussive events result in substance P release and subsequent hyperphosphorylation of tau. Neuronal sensory fibres surrounding blood vessels undergo stretch in response to a concussive event. The resultant mechanical stimulation activates mechanoreceptors and triggers substance P release. Substance P binds to its receptors, activating an array of kinases known to be associated with hyperphosphorylation of tau. Hyperphosphorylation of tau destabilises microtubules and results in neurofibrillary tangles.

Having established that substance P antagonists inhibit tau hyperphosphorylation after concussive injury, we propose that the mechanism by which this occurs is through substance P binding to its NK1 receptor and activating various biochemical enzymes (kinases) that will result in the hyperphosphorylation of tau and the development of chronic traumatic encephalopathy (CTE). The mechanism of this activation is shown in FIG. 4. Activation of mechanoreceptors during concussive injury causes the release of substance P (example 2 and Ang et al., 2011, PLoS One 6, e24535). Furthermore the extent of the substance P release and the activation of its receptors is proportional to the frequency of the stimulation (Mantyh, 2002, J. Clin. Psychiatry 63, 6-10). Specifically, repeated exposure to a SP-releasing mechanical stimulus such as concussion increases expression of the substance P receptors for a prolonged period (>8 days), leading to more potent activation of adjacent substance P receptor expressing neurons. Furthermore, repeated stimulation leads to greater substance P release, resulting in greater diffusion of substance P away from the perivascular site of release and the stimulation of more distant neurons. It has been estimated that approximately 3-5 times more neurons are activated in response to more frequent stimulation (Mantyh, 2002, J. Clin. Psychiatry 63, 6-10). As shown by us in example 3, administration of a substance P receptor antagonist prevents the activation of the substance P receptor, prevents the activation of enzymes responsible for tau hyperphosphorylation, and thus prevents such tau hyperphosphorylation and the development/progression of chronic traumatic encephalopathy.

Example 5

Concussion Results in the Greatest Mechanical Stress at the Base of Sulci

Figure 5:
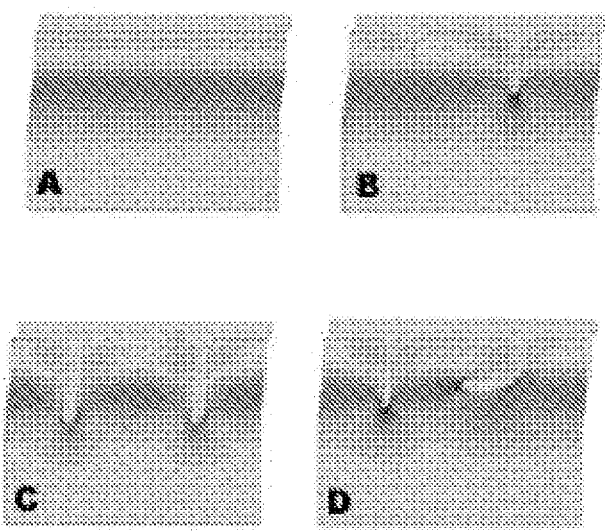
FIG. 5 shows stress fields following simulated rotational acceleration in models replicating brain tissue with no sulci (A) to brain tissue with complex sulci formation (3-D). Higher stress is indicated as black and is focused at the base of the sulci irrespective of the sulcus morphology.

Having established that both release of substance P and accumulation of hyperphosphorylated tau occurred following a concussive event, it remained to be shown why accumulation of hyperphosphorylated tau in human CTE was prominent at the base of the brain sulci. We have shown in example two that substance P release occurs in response to stimulation of mechanoreceptors on sensory nerve fibres. One highly innovative step in the current disclosure is the realization that in gyrencephalic animals, including man, sulci protect the brain cortex from mechanical injury by focusing the stress points to the base of the sulci. This is best illustrated in models of brain tissue that both incorporate and exclude sulci within them, and subsequently simulating the effects of mechanical stress (Cloots et al., 2008, Ann. Biomed. Eng. 36, 1203-1215). The simulation of the effects of mechanical strain typical of rotational acceleration in models replicating the brain tissue with and without sulci is shown in FIG. 5. Higher mechanical stress is indicated as black. These results clearly show that the addition of sulci to the model focuses the stress to the base of the sulci, irrespective of the sulcus morphology. This mechanical stress pattern is remarkably similar to the post-mortem localisation of hyperphosphorylated tau reported in CTE and shown in FIG. 1.

This example confirms that in a gyrencephalic brain, exposure to a mechanical concussive event will focus the mechanical forces to the base of the sulci, thereby preferentially activating mechanoreceptors on sensory nerves in that location. Example 2 has already shown that activation of mechanoreceptors on sensory nerve fibres will cause the perivascular release of substance P.

The claims defining the invention are as follows:

1. A method of inhibiting tau hyperphosphorylation in a chronic traumatic encephalopathy (CTE) subject in need thereof, comprising:
   selecting a subject diagnosed with CTE, and
   administering to the subject a substance P receptor antagonist in an amount effective to inhibit tau hyperphosphorylation in the subject, wherein the substance P receptor antagonist is a NK1 receptor antagonist.

2. A method according to claim 1, wherein the substance P receptor antagonist is administered to the subject at a dose of 0.25 mg/kg to 25 mg/kg.

3. A method according to claim 1, wherein the NK1 receptor antagonist is one or more selected from the group consisting of Casopitant, CGP49823, CP-122,721, CP-96,345, CP-99,994, FK 888, GR 82334, GR 94800, GR203040, GR-205171, GSK1144814, GSK206136, GSK424887, GW679769, HSP-117, L 703,606, L 732,138, L 733,060, L 742,694, L668,169, LY 303241, LY 303870, LY 306740, Maropitant, MEN 11149, Orvepitant, PD 154075, R-544, RP-67580, RPR 100893, SCH619734, Spantide II, Spantide III, Spendide, SR140333, Vestipitant, WIN-41,708, WIN-62,577, and pharmaceutically acceptable salts thereof.

4. A method according to claim 1, wherein the subject has suffered multiple concussive events.

5. A method of inhibiting tau hyperphosphorylation in a chronic traumatic encephalopathy (CTE) subject that has suffered multiple concussive events, comprising:
   selecting a subject diagnosed with CTE and having suffered multiple concussive events, and
   administering to the subject Casopitant at a dose of from 0.25 mg/kg to 25 mg/kg effective to inhibit tau hyperphosphorylation in the subject.

* * * * *